US007638538B1

(12) United States Patent
Arkinstall et al.

(10) Patent No.: US 7,638,538 B1
(45) Date of Patent: Dec. 29, 2009

(54) PHARMACEUTICALLY ACTIVE SULFONYL AMINO ACID DERIVATIVES

(75) Inventors: Stephen Arkinstall, Belmont, MA (US); Serge Halazy, Vetraz-Monthoux (FR); Dennis Church, Commugny (CH); Montserrat Camps, Versoix (CH); Thomas Rueckle, Plan-les-Ouates (CH); Jean-Pierre Gotteland, Beaumont (FR); Marco Biamonte, San Diego, CA (US)

(73) Assignee: Laboratoires Serono S.A., Coinsins (CH)

( * ) Notice: Subject to any disclaimer, the term of this patent is extended or adjusted under 35 U.S.C. 154(b) by 0 days.

(21) Appl. No.: 10/088,090

(22) PCT Filed: Sep. 28, 2000

(86) PCT No.: PCT/IB00/01382

§ 371 (c)(1),
(2), (4) Date: Jun. 21, 2002

(87) PCT Pub. No.: WO01/23379

PCT Pub. Date: Apr. 5, 2001

(30) Foreign Application Priority Data

Sep. 28, 1999 (EP) .................................. 99810871

(51) Int. Cl.
*A61K 31/44* (2006.01)
*C07D 409/12* (2006.01)
(52) U.S. Cl. ..................... 514/336; 546/280.4
(58) Field of Classification Search .................. 514/322, 514/342, 351, 445, 336; 546/199, 272.7, 546/280.4, 293, 193; 549/62
See application file for complete search history.

(56) References Cited

U.S. PATENT DOCUMENTS

| 3,396,030 | A  | * | 8/1968  | Haas et al. ................... 430/627 |
| 6,172,261 | B1 | * | 1/2001  | Vermeulin et al. ............. 564/84  |
| 6,503,901 | B1 | * | 1/2003  | Thompson et al. ........... 514/221    |
| 6,646,149 | B1 | * | 11/2003 | Vermeulin et al. ............ 560/25   |

FOREIGN PATENT DOCUMENTS

| EP | 0 757 984  |   | 2/1997  |
| EP | 1085011    | * | 3/2001  |
| FR | 2 312 242  |   | 12/1976 |
| JP | 11 236369  |   | 9/1999  |
| JP | 11 246527  |   | 9/1999  |
| WO | 98 03166   |   | 1/1998  |
| WO | 98 39329   |   | 9/1998  |
| WO | 98 49188   |   | 11/1998 |
| WO | 99 42443   |   | 8/1999  |

OTHER PUBLICATIONS

Okamoto et al. "Lysine derivative and proteinase inhibitor" CA 105:97950 (1986).*
CAS RN 150-13-0.*
Bozyczko-Coyne et al. "Targeting the JNK pathway . . . " PMID;12769633 (2002).*
Wilbraham et al. "Organic and biological chemistry" S, Ill. Univ. p. 222-225 (1985).*
Arkinstall "preparation o N-arylsulfonyl amino acid . . . " CA 134:266198 (2001).*
Autoimmune diseases Medical dictionary online (1997).*
Baker Botts "Reach through claims" (2002).*
Trilateral project B3b "comparative stuy on reach through claims" (2001).*
Exhibit I.*
Kumagae et al. "Human c-Jun . . . " Mole. Brain Res. v.67, p. 10-17 (1999).*
Shau et al. "The crystal . . . " J. Mo. Biol. v.383, p. 885-893 (2008).*
Scapin et al. "The structure of JNK3 . . . " Chem. & Biol. v.10, p. 705-712 (2003).*
Ragab A. El-Sayed: "A facile synthesis and some new reactions of N-benzylcarboxamides with essential amino acids" Indian J. Chem., 37B(10), pp. 1059-1062 1998.
Ragab A. El-Sayed: "A comparative study of the reactions of thiophene-2-carboxanilides and related compounds" J. Serb. Chem. Soc., 63(5), pp. 371-377 1998.
M.H. El-Hakim: "Synthesis and antimicrobial activity of some new 2- and 4-chlorobenzanilide p-sulfonylamino acid and dipeptide derivatives".
Ragab A. El-Sayed: "Some novel sulfanilyl amino acid derivatives" J. Serb. Chem. Soc., 56(6), pp. 311-318 1991.
Xiaoling Xie et al.: "Crystal structure of JNK3: a kinase implicated in neuronal apoptosis" Structure, 6 (8), pp. 983-991 1998.
Derek D. Yang et al.: "Absence of excitotoxicity-induced apoptosis in the hippocampus of mice lacking the Jnk3 gene" Nature, 389 (6653), pp. 865-870 1997.
Derek D. Yang et al.: "Differentiation of DC4+ T Cells to Th- cells requires MAP kinase JNK2" Immunity, 9, pp. 575-585 1998.
Kanaga Sabapathy et al.: "JKN2 is required for efficient T-cell activation and apoptosis but not for normal lymphocyte development" Current Biology, 9, pp. 116-125 1999.
Yoshihiro Kumagae et al.: "Human c-Jun N-terminal kinase expression and activation in the nervous system" Brain Res. Mol. Brain Res., 67(1), pp. 10-17 1999.
U.S. Appl. No. 10/088,074, filed Mar. 20, 2002, Arkinstall, et al.
U.S. Appl. No. 10/070,954, filed Mar. 13, 2002.
U.S. Appl. No. 12/142,296, filed Jun. 19, 2008, Halazy, et al.

* cited by examiner (Continued)

*Primary Examiner*—Celia Chang
(74) *Attorney, Agent, or Firm*—Oblon, Spivak, McClelland, Maier & Neustadt, L.L.P.

(57) ABSTRACT

The present invention is related to sulfonyl amino acid derivatives of formula (I), notably for use as pharmaceutically active compounds, as well as to pharmaceutical formulations containing such sulfonyl amino acid derivatives. Said sulfonyl amino acid are efficient modulators of the JNK pathway, they are in particular efficient inhibitors of JNK 2 and 33. The present invention is furthermore related to novel sulfonyl amino acid derivatives as well as to methods of their preparation.

(I)

$$Ar^1 \underset{X}{\overset{\|}{\underset{R^1}{N}}} (CH_2)_n - Ar^2 - SO_2 - \underset{R^2}{\overset{R^3}{N}} \underset{R^4}{\overset{R^5}{\underset{O}{N}}} N \underset{R^6}{\diagdown}$$

4 Claims, No Drawings

PHARMACEUTICALLY ACTIVE SULFONYL AMINO ACID DERIVATIVES

FIELD OF THE INVENTION

The present invention is related to sulfonyl amino acid derivatives notably for use as pharmaceutically active compounds, as well as pharmaceutical formulations containing such sulfonyl amino acid derivatives. In particular, the present invention is related to sulfonyl dipeptide derivatives displaying a substantial modulatory, notably an inhibitory activity of the JNK (Jun-Kinase) function or pathways respectively, and which are therefore particularly useful in the treatment and/or prevention of disorders of the autoimmune and the neuronal system. The present invention is furthermore related to novel sulfonyl amino acid derivatives as well as methods of their preparation.

BACKGROUND OF THE INVENTION

Apoptosis denotes the complex contortions of the membrane and organelles of a cell as it undergoes the process of programmed cell death. During said process, the cell activates an intrinsic suicide program and systematically destroys itself. The following series of events can be observed:

The cell surface begins to bleb and expresses pro-phagocytic signals. The whole apoptotic cell then fragments into membrane-bound vesicles that are rapidly and neatly disposed of by phagocytosis, so that there is minimised damage to the surrounding tissue.

The cell then separates from its neighbors.

The nucleus also goes through a characteristic pattern of morphological changes as it commits genetic suicide, the chromatin condenses and is specifically cleaved to fragments of DNA.

Neuronal cell death plays an important role in ensuring that the nervous system develops normally. It appears that the death of developing neurones depends on the size of the target that they innervate: cells with fewer synaptic partners are more likely to die than those that have formed multiple synapses. This may reflect a process, which balances the relative number of pre- to postsynaptic neurones in the developing nervous system. Although neuronal cell death was assumed to be apoptotic, it was only recently that neurones in developing rodent brain were conclusively shown to undergo apoptosis as classified by morphology and DNA fragmentation. As cell death during development is clearly not a pathological process, it makes sense that cells actually cease to exist.

Neuronal death occurs via either apoptotic or necrotic processes following traumatic nerve injury or during neurodegenerative diseases. Multiple components are emerging as key players having a role in driving neuronal programmed cell death. Amongst the components leading to neuronal apoptosis are members of the SAPK/JNK being a subfamily of MAP Kinases (MAPKs).

MAPKs (mitogen-activated protein kinases) are serine/threonine kinases that are activated by dual phosphorylation on threonine and tyrosine residues. In mammalian cells, there are at least three separate but parallel pathways that convey information generated by extracellular stimuli to the MAPKs. Said pathways consist of kinase cascades leading to activation of the ERKs (extracellular regulated kinases), the JNKs (c-Jun N-terminal kinases), and the p38/CSBP kinases. While both the JNK and p38 pathways are involved in relaying stress-type extramolecular signals, the ERK pathway is primarily responsible for transducing mitogenic/differentiation signals to the cell nucleus.

SAPK cascades represent a sub-family of the mitogen-activating protein kinase family, that are activated by different external stimuli including DNA damage following UV irradiation, TNF-α, IL-1β, ceramide, cellular stress, and reactive oxygen species and have distinct substrate specificities. Signal transduction via MKK4/JNK of MKK3/p38 results in the phosphorylation of inducible transcription factors, c-Jun and ATF2, which then act as either homodimers or heterodimers to initiate transcription of down-stream effectors.

c-Jun is a protein that is forming homodimers and heterodimers (with e.g. c-Fos) to produce the transactivating complex AP—which is required for the activation of many genes (e.g. matrix metalloproteinases) involved in the inflammatory response. The JNKs were discovered when it was found that several different stimuli such as UV light and TNF-α stimulated phosphorylation of c-Jun on specific serine residues in the N-terminus of the protein.

In a recent publication of Xie X et al, (*Structure* 1998, 6 (8); 983-991) it has been suggested that activation of stress-activated signal transduction pathways are required for neuronal apoptosis induced by NGF withdrawal in rat PC-12 and superior cervical ganglia (SCG) sympathetic neuronal cells. Inhibition of specific kinases, namely MAP kinase kinase 3 (MKK3) and MAP kinase kinase 4 (MKK4), or c-Jun (part of the MKK-4 cascade) may be sufficient to block apoptosis (see also Kumagae Y et al, in *Brain Res Mol Brain Res*, 1999, 67(1), 10-17 and Yang D D et al in *Nature*, 1997, 389 (6653); 865-870). Within a few hours of NGF deprivation in SCG neurones, c-Jun becomes highly phosphorylated and protein levels increase. Similarly in rat PC-12 cells deprived of NGF, JNK and p38 undergo sustained activation while ERKs are inhibited. Consistent with this JNK3 KO mice are resistant to excitotoxicity induced apoptosis in the hippocampus and more importantly they display greatly reduced epileptic like seizures in response to excitotoxicity as compared to normal animals (*Nature* 1997, 389, 865-870).

More recently, it has been reported that the JNK signalling pathway is implicated in cell proliferation and could play an important role in autoimmune diseases (*Immunity*, 1998, 9, 575-585; *Current Biology*, 1999, 3, 116-125) which are mediated by T-cell activation and proliferation.

Naive (precursor) CD4+ helper T (Th) cells recognise specific MHC-peptide complexes on antigen-presenting cells (APC) via the T-cell receptor (TCR) complex. In addition to the TCT-mediated signal, a costimulatory signal is provided at least partially by the ligation of CD28 expressed on T-cells with B7 proteins on APC. The combination of these two signals induces T-cell clonal expression.

After 4-5 days of proliferation, precursor CD4+ T cells differentiate into armed effector Th cells that mediate the functions of the immune system. During the differentiation process, substantial reprogramming of gene expression occurs.

Two subsets of effector Th cells have been defined on the basis of their distinct cytokine secretion pattern and their immunomodulatory effects: Th1 cells produce IFNγ and LT (TNF-β), which are required for cell-mediated inflammatory reactions; Th2 cells secrete IL-4, IL-5, IL-6, IL-10 and IL13, which mediate B cell activation and differentiation. These cells play a central role in the immune response. The JNK MAP Kinase pathway is induced in Th1 but not in Th2 effector cells upon antigen stimulation. Furthermore, the differentiation of precursor CD4+ T cells into effector Th1 but not Th2 cells is impaired in JNK2-deficient mice. Therefore, in recent years it has been realized that the JNK kinase pathway plays an important role in the balance of Th1 and TH2 immune response through JNK2.

With the objective of inhibiting the JNK kinase pathway, WO/9849188 teaches the use of a human polypeptide, i.e. JNK-interacting protein 1 (JIP-1), which is a biological product and which has also been assayed for overcoming apoptosis related disorders.

Although such human polypeptides have been confirmed to have an inhibitory effect onto the JNK kinase pathway, a whole variety of drawbacks are associated with their use:

Active bio-peptides or bio-proteins are only obtained by means of rather comprehensive and expensive bio-synthesis which consequently frequently renders the resulting products finely cost-intensive.

The peptides are known to display poor membrane penetration and may not cross the blood brain membrane, The principal drawback to the use of peptide inhibitors or antagonists is the problem of low oral bioavailability resulting from intestinal degradation. Hence, they must be administered parenterally and finally, peptide inhibitors or antagonists are frequently viewed by the host body as intruding material to be eliminated, thus setting off an auto-immune response.

Hence, it is an objective of the present invention to provide relatively small molecules that avoid essentially all of the above-mentioned drawbacks arising from the use of peptides or proteins, however, which are suitable for the treatment of a variety of diseases, in particular of neuronal or the autoimmune system related disorders. It is notably an objective of the present invention to provide relatively small molecule chemical compounds which are able to modulate, preferably to down-regulate or to inhibit the JNK (Jun kinase) pathway so to be available as a convenient method of treating diseases which are preferably mediated by the JNK function. Moreover, it is an objective of the present invention to provide methods for preparing said small molecule chemical compounds. It is furthermore an objective of the present invention to provide a new category of pharmaceutical formulations for the treatment of diseases, preferably mediated by the JNK function. It is finally an objective of the present invention to provide a method for the treatment and/or prevention of diseases that are caused by disorders of the autoimmune and/or the neuronal system.

DESCRIPTION OF THE INVENTION

The aforementioned objectives have been met according to the independent claims. Preferred embodiments are set out within the dependent claims which are incorporated herewith.

The following paragraphs provide definitions of the various chemical moieties that make up the compounds according to the invention and are intended to apply uniformly throughout the specification and claims unless an otherwise expressly set out definition provides a broader definition.

"$C_1$-$C_6$-alkyl" refers to monovalent alkyl groups having 1 to 6 carbon atoms. This term is exemplified by groups such as methyl, ethyl, n-propyl, isopropyl, n-butyl, isobutyl, tert-butyl, n-hexyl and the like.

"Aryl" refers to an unsaturated aromatic carbocyclic group of from 6 to 14 carbon atoms having a single ring (e.g. phenyl) or multiple condensed rings (e.g. naphthyl). Preferred aryl include phenyl, naphthyl, phenantrenyl and the like.

"$C_1$-$C_6$-alkyl aryl" refers to $C_1$-$C_6$-alkyl groups having an aryl substituent, including benzyl, phenethyl and the like.

"Heteroaryl" refers to a monocyclic heteroaromatic, or a bicyclic or a tricyclic fused-ring heteroaromatic group. Particular examples of heteroaromatic groups include optionally substituted pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetra-hydroisoquinolyl, purinyl, pteridinyl, carbazolyl, xanthenyl or benzoquinolyl.

"$C_1$-$C_6$-alkyl heteroaryl" refers to $C_1$-$C_6$-alkyl groups having a heteroaryl substituent, including 2-furylmethyl, 2-thienylmethyl, 2-(1H-indol-3-yl)ethyl and the like.

"Alkenyl" refers to alkenyl groups preferably having from 2 to 6 carbon atoms and having at least 1 to 2 sites of alkenyl unsaturation. Preferable alkenyl groups include ethenyl(—CH=$CH_2$), n-2-propenyl (allyl, —$CH_2$CH=$CH_2$) and the like.

"Alkynyl" refers to alkynyl groups preferably having from 2 to 6 carbon atoms and having at least 1-2 sites of alkynyl unsaturation, preferred alkynyl groups include ethynyl (—C≡CH), propargyl (—$CH_2$C≡CH), and the like.

"Acyl" refers to the group —C(O)R where R includes "$C_1$-$C_6$-alkyl", "aryl", "heteroaryl", "$C_1$-$C_6$-alkyl aryl" or "$C_1$-$C_6$-alkyl heteroaryl".

"Acyloxy" refers to the group —OC(O)R where R includes "$C_1$-$C_6$-alkyl", "aryl", "heteroaryl", "$C_1$-$C_6$-alkyl aryl" or "$C_1$-$C_6$-alkenyl heteroaryl".

"Alkoxy" refers to the group —O—R where R includes "$C_1$-$C_6$-alkyl" or "aryl" or "heteroaryl" or "$C_1$-$C_6$-alkyl aryl" or "$C_1$-$C_6$-alkyl heteroaryl". Preferred alkoxy groups include by way of example, methoxy, ethoxy, phenoxy and the like.

"Alkoxycarbonyl" refers to the group —C(O)OR where R includes "$C_1$-$C_6$-alkyl" or "aryl" or "heteroaryl" or "$C_1$-$C_6$-alkyl aryl" or "$C_1$-$C_6$-alkyl heteroaryl".

"Aminocarbonyl" refers to the group —C(O)NRR' where each R, R' includes independently hydrogen or $C_1$-$C_6$-alkyl or aryl or heteroaryl or "$C_1$-$C_6$-alkyl aryl" or "$C_1$-$C_6$-alkyl heteroaryl".

"Acylamino" refers to the group —NR(CO)R' where each R, R' is independently hydrogen or "$C_1$-$C_6$-alkyl" or "aryl" or "heteroaryl" or "$C_1$-$C_6$-alkyl aryl" or "$C_1$-$C_6$-alkyl heteroaryl".

"Halogen" refers to fluoro, chloro, bromo and iodo atoms.

"Sulfonyl" refers to group "—$SO_2$—R" wherein R is selected from H, "aryl", "heteroaryl", "$C_1$-$C_6$-alkyl", "$C_1$-$C_6$-alkyl" substituted with halogens e.g. an —$SO_2$—$CF_3$ group, "$C_1$-$C_6$-alkyl aryl" or "$C_1$-$C_6$-alkyl heteroaryl".

"Sulfoxy" refers to a group "—S(O)—R" wherein R is selected from H, "$C_1$-$C_6$-alkyl", "$C_1$-$C_6$-alkyl" substituted with halogens e.g. an —SO—$CF_3$ group, "aryl", "heteroaryl", "$C_1$-$C_6$-alkyl aryl" or "$C_1$-$C_6$-alkyl heteroaryl".

"Thioalkoxy" refers to groups —S—R where R includes "$C_1$-$C_6$-alkyl" or "aryl" or "heteroaryl" or "$C_1$-$C_6$-alkyl aryl" or "$C_1$-$C_6$-alkyl heteroaryl". Preferred thioalkoxy groups include thiomethoxy, thioethoxy, and the like.

"Substituted or unsubstituted": Unless otherwise constrained by the definition of the individual substituent, the above set out groups, like "alkyl", "alkenyl", "alkynyl", "aryl" and "heteroaryl" etc. groups can optionally be substituted with from 1 to 5 substituents selected from the group consisting of "$C_1$-$C_6$-alkyl", "$C_1$-$C_6$-alkyl aryl", "$C_1$-$C_6$-alkyl heteroaryl", "$C_2$-$C_6$-alkenyl", "$C_2$-$C_6$-alkynyl", primary, secondary or tertiary amino groups or quarter-nary ammonium moieties, "acyl", "acyloxy", "acylamino", "aminocarbonyl", "alkoxycarbonyl", "aryl", "heteroaryl", carboxyl, cyano, halogen, hydroxy, mercapto, nitro, sulfoxy, sulfonyl, alkoxy, thioalkoxy, trihalomethyl and the like. Alternatively said substitution could also comprise situations where neighboring substituents have undergone ring closure, notably when viccinal functional substituents are involved, thus forming e.g. lactams, lactons, cyclic anhydrides, but also acetals, thioacetals, animals formed by ring closure for instance in an effort to obtain a protective group.

"Pharmaceutically acceptable salts or complexes" refers to salts or complexes of the below-identified compounds of formula I that retain the desired biological activity. Examples of such salts include, but are not restricted to acid addition salts formed with inorganic acids (e.g. hydrochloric acid, hydrobromic acid, sulfuric acid, phosphoric acid, nitric acid, and the like), and salts formed with organic acids such as acetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, naphthalene disulfonic acid, and polygalacturonic acid. Said compounds can also be administered as pharmaceutically acceptable quaternary salts known by a person skilled in the art, which specifically include the quarternary ammonium salt of the formula —NR,R',R"+Z−, wherein R, R', R" is independently hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, fumarate, citrate, tartrate, ascrobate, cinnamoate, mandeloate, and dipheylacetate).

"Pharmaceutically active derivative" refers to any compound that upon administration to the recipient, is capable of providing directly or indirectly, the activity disclosed herein.

"Enantiomeric excess" (ee) refers to the products that are obtained by an essentially enantiomeric synthesis or a synthesis comprising an enantioselective step, whereby a surplus of one embodiment in the order of at least about 52% ee is yielded. In the absence of an enantiomeric synthesis, racemic products are usually obtained that do however also have the inventive set out activity as JunK2 and/or 3 inhibitors.

Quite surprisingly, it was now found that sulfonyl amino acid derivatives according to formula I are suitable pharmaceutically active agents, by effectively inhibiting the action of JNKs, notably, JNK 2 and 3. In terms of application convenience, the inventively found compounds displays a marked superiority compared to the above mentioned peptide or protein approach as they are also accessible to oral administration. They could be prescribed by a physician and require only minor supervision. Also, the inventively found compounds are available at lower costs compared to said peptide compounds described hitherto.

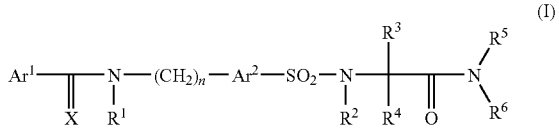

Ar$^1$ and Ar$^2$ are independently from each other substituted or unsubstituted aryl or heteroaryl groups, X is O or S, preferably O;

R$^1$ is hydrogen or an unsubstituted or substituted C$_1$-C$_6$-alkyl group, preferably H.

Alternatively R$^1$ could form a substituted or unsubstituted 5-6-membered saturated or unsaturated fused ring with Ar$^1$.

According to a further alternative R$^2$ and R$^4$ could form a substituted or unsubstituted 5-6-membered saturated or non-saturated ring.

R$^2$ is hydrogen or a substituted or unsubstituted C$_1$-C$_6$-alkyl group, preferably H.

n is an integer from 0 to 5, preferably between 1-3 and most preferred 1.

R$^3$ and R$^4$ are independently from each other selected from the group comprising or consisting of natural or synthetic amino acid residues, hydrogen, substituted or unsubstituted C$_1$-C$_6$-alkyl, like trihalomethyl, substituted or unsubstituted C$_1$-C$_6$-alkoxy, NH$_2$, SH, C$_1$-C$_6$-thioalkyl, acylamino, aminocarbonyl, substituted or unsubstituted C$_1$-C$_6$-alkoxycarbonyl, aryl, heteroaryl, substituted or unsubstituted 4-8-membered cyclic alkyl, optionally containing 1-3 heteroatoms, carboxyl, cyano, halogen, hydroxy, nitro, acyloxy, sulfoxy, sulfonyl, C$_1$-C$_6$-thioalkoxy, whereby though, at least one of R$^3$ and/or R$^4$ must be an amino acid residue.

R$^5$ is H or substituted or unsubstituted C$_1$-C$_6$-alkyl.

R$^6$ is selected from the group comprising or consisting of H, substituted or unsubstituted C$_1$-C$_6$-aliphatic alkyl, substituted or unsubstituted saturated cyclic C$_4$-C$_8$-alkyl optionally containing 1-3 heteroatoms and optionally fused with an aryl or heteroaryl; or R$^6$ is a substituted or unsubstituted aryl, substituted or unsubstituted heteroaryl.

Thereby, the aryl or heteroaryl groups of R$^6$ are optionally substituted by substituted or unsubstituted C$_1$-C$_6$- alkyl, like trihalomethyl, substituted or unsubstituted C$_1$-C$_6$-alkoxy, substituted or unsubstituted C$_2$-C$_6$-alkenyl, substituted or unsubstituted C$_2$-C$_6$-alkynyl, amino, acylamino, aminocarbonyl, substituted or unsubstituted C$_1$-C$_6$-alkoxycarbonyl, aryl, carboxyl, cyano, halogen, hydroxy, nitro, sulfonyl, sulfoxy, C$_1$-C$_6$-thioalkoxy.

Alternatively, R$^5$ and R$^6$ taken together could form a substituted or unsubstituted 4-8-membered saturated cyclic alkyl or heteroalkyl group.

The present invention also includes the geometrical isomers, the optical active forms, enantiomers, diastereomers of compounds according to formula I, as well as their racemates and also pharmaceutically acceptable salts as well as the pharmaceutically active derivatives of the sulfonyl amino acid derivatives of formula I.

According to a preferred embodiment, at least one of R$^3$ and/or R$^4$ is selected from the group consisting of the following natural amino acid residues: alanyl, arginyl, asparaginyl, aspartyl, cysteinyl, glutaminyl, glutamyl, glycyl, histidyl, isoleucyl, leucyl, lysyl, methionyl, phenylalanyl, prolyl, seryl, threonyl, tryptophanyl, tyrosyl, valyl.

According to a preferred embodiment, Ar$^1$ and Ar$^2$ are independently selected from the group comprising or consisting of phenyl, thienyl, furyl, pyridyl. Said residues are optionally substituted by at least one substituted or unsubstituted C$_1$-C$_6$alkyl, like trihalomethyl, substituted or unsubstituted C$_1$-C$_6$-alkoxy, substituted or unsubstituted C$_2$-C$_6$-alkenyl, substituted or unsubstituted C$_2$-C$_6$-alkynyl, amino, acylamino, aminocarbonyl, substituted or unsubstituted C$_1$-C$_6$-alkoxycarbonyl, aryl, carboxyl, cyano, halogen, hydroxy, nitro, sulfoxy, sulfonyl, acyloxy, substituted or unsubstituted C$_1$-C$_6$-thioalkoxy. In a particularly preferred embodiment Ar$^1$ in an unsubstituted or substituted phenyl and Ar$^2$ is a thienyl group.

In preferred sulfonyl amino acid derivatives according to formula I, Ar$^1$ is an unsubstituted or substituted phenyl, preferably a 4-chlorophenyl group, X is preferably O, R$^1$, R$^2$, R$^3$ and R$^4$ are preferably hydrogen, n is 1, Ar$^2$ is preferably thienyl, R$^5$ is H or C$_1$-C$_6$-alkyl.

In said preferred embodiment, $R^6$ is selected from the group comprising or consisting of H, a substituted or unsubstituted $C_1$-$C_6$-aliphatic alkyl—e.g. a $C_1$-$C_6$-alkylamino aryl, a $C_1$-$C_6$-alkylamino heteroaryl, a substituted or unsubstituted cyclic $C_4$-$C_8$-alkyl containing optionally 1-3 heteroatoms and being optionally fused with an unsubstituted or substituted aryl or heteroaryl; or $R^6$ is an unsubstituted or substituted aryl or heteroaryl.

The above mentioned aryl or heteroaryl groups are optionally substituted by substituted or unsubstituted $C_1$-$C_6$-alkyl, like trihalomethyl, substituted or unsubstituted $C_1$-$C_6$-alkoxy, substituted or unsubstituted $C_2$-$C_6$-alkenyl, substituted or unsubstituted $C_2$-$C_6$-alkynyl, amino, acylamino, aminocarbonyl, substituted or unsubstituted $C_1$-$C_6$-alkoxycarbonyl, aryl, carboxyl, cyano, halogen, hydroxy, nitro, acyloxy, sulfoxy, sulfonyl, $C_1$-$C_6$-thioalkoxy.

Alternatively, $R^5$ and $R^6$ taken together could form an unsubstituted or substituted 4-8-membered saturated cyclic alkyl or heteroalkyl group, e.g. an unsubstituted or substituted piperidino group.

A particularly preferred embodiment of the present invention is related to those sulfonyl amino acid derivatives, wherein $R^5$ is H; and $R^6$ is a $C_1$-$C_6$-alkyl which is substituted by an aryl, an heteroaryl group or an aminoaryl, aminoheteroaryl, aryloxy, heteroaryloxy, whereby said aryl and heteroaryl groups are optionally substituted by substituted or unsubstituted $C_1$-$C_6$-alkyl, like trihalomethyl, substituted or unsubstituted $C_1$-$C_6$-alkoxy, substituted or unsubstituted $C_2$-$C_6$-alkenyl, substituted or unsubstituted $C_2$-$C_6$-alkynyl, amino, acylamino, aminocarbonyl, substituted or unsubstituted $C_1$-$C_6$-alkoxycarbonyl, substituted or unsubstituted aryl, carboxyl, cyano, halogen, hydroxy, nitro, sulfoxy, sulfonyl, acryloxy, $C_1$-$C_6$-thioalkoxy.

In a further preferred embodiment of the present invention, $R^6$ of the sulfonyl amino acid derivatives is a substituted or unsubstituted pyridyl group.

Specific examples of compounds of formula I include the following:

4-chloro-N-({5-[({2-[(2-{[3-chloro-5-(trifluoromethyl)pyridin-2-yl]amino}ethyl)amino]-2-oxoethyl}amino)sulfonyl]thien-2-yl}methyl)benzamide 4-chloro-N-[(5-{[(2-{[2-({5-nitropyridin-2-yl}amino)ethyl]amino}-2-oxoethyl)amino]sulfonyl}thien-2-yl)methyl]benzamide 4-chloro-N-({5-[({2-oxo-2-[(2-{[3-(trifluoromethyl)pyridin-2-yl]amino}ethyl)amino]ethyl}amino)sulfonyl]thien-2-yl}methyl)benzamide 4-chloro-N-({5-[({2-oxo-2-[(2-{[5-(trifluoromethyl)pyridin-2-yl]amino}ethyl)amino]ethyl}amino)sulfonyl]thien-2-yl}methyl)benzamide N-({5-[({2-[4-(1H-1,2,3-benzotriazol-1-yl)pipierdin-1-yl]-2-oxoethyl}amino)sulfonyl]thien-2-yl}methyl)-4-chlorobenzamide 4-chloro-N-[(5-{[(2-oxo-2-{3-[(trifluoromethyl)sulfonyl]anilino}ethyl)amino]sulfonyl}thien-2-yl)methyl]benzamide A further aspect of the present invention consists in the use of the sulfonyl amino acid derivatives according to formula I for the preparation of pharmaceutical compositions for the modulation—notably for the down-regulation, e.g. up to the inhibition—of the JNK function or signalling pathway associated disorders, in particular against neuronal disorders and/or against disorders of the immune system as well as said pharmaceutical compositions themselves. Preferred JNK pathways are the JNK1 and/or JNK2 and/or JNK3.

As above pointed out, the compounds of formula I are suitable to be used as a medicament. Some very few of the compounds falling into the above generic formula I have been disclosed prior to the filing of the present application, but no medical or biological activity whatsoever was unveiled so far. Hence, it is herein reported that both the novel and the few know compounds falling under the above set out generic formula I are indeed suitable for use in treating a whole variety of diseases, like disorders of the autoimmune system and neuronal system of mammals, notably of human beings. More specifically, the compounds according to formula I, alone or in the form of a pharmaceutical composition, are useful for the modulation of the JNK pathway, more specifically for treatment or prevention of disorders associated with abnormal expression or activity of JNK, notably of JNK1 and/or JNK2 and/or JNK3. Said modulation usually preferably involves the inhibition of the JNK pathways, notably of the JNK1 and/or JNK2 and/or JNK3. Such an abnormal expression or activity of JNK could be triggered by numerous stimuli (e.g. stress, septic shock, oxidative stress, cytokines) and could lead to out-of-control apoptosis or autoimmune diseases that is frequency involved in the below enumerated disorders and disease states. Hence, the compounds according to formula I could be used for the treatment of disorders by modulating the JNK function or signalling pathways. Said modulation of the JNK function or pathways could involve its activation, but preferably it involves the down-regulation up to inhibition of the JNK pathways, notably of the JNK1 and/or JNK2 and/or JNK3. The compounds according to formula I could be employed alone or in combination with further pharmaceutical agents.

Specifically, the compounds pursuant to formula I are useful for the treatment or prevention of immuno- and/or neuronal-related diseases or pathological states in which inhibition of JNK1 and/or JNK2 and/or JNK3 plays a critical role such as epilepsy; neurodegenerative diseases including Alzheimer's disease, Huntingdon's disease, Parkinson's disease; retinal diseases; spinal cord injury; head trauma, autoimmune diseases including multiple Sclerosis, inflammatory bowel diseases (IBD), rheumatoid arthritis; asthma; septic shock; transplant rejection; cancers including breast, colorectal, pancreatic and cardiovascular diseases including stroke, cerebral ischemia, arterosclerosis, myocordial infarction, myocordial reperfusion injury.

Quite surprisingly it turned out that the inventively found compounds according to formula I do show a considerable activity as inhibitors of JNK1 and/or JNK2 and/or JNK3. In a preferred embodiment, the compounds according to the invention are unexpectedly essentially inactive in view of 2 further apoptosis modulating enzymes, i.e. p38 and ERK2—belonging incidentally to the same family as JNK2 and 3. Hence, the compounds according to the present invention provide the outstanding possibility to treat selectively disorders related to the JNK pathways, while being essentially inefficient with regard to other targets like said p38 and ERK2, so that they could indeed be viewed as selective inhibitors. This is of considerable significance, as these related enzymes are generally involved in different disorders, so that for the treatment of a distinct disorder, it is desired to employ a correspondingly selective medicament.

As a matter of fact, prior to the herein reported, surprisingly found sulfonyl amino acid derivatives according to formula I, nothing was known in respect of the use of small molecule chemical compounds as inhibitors of the JNK pathway.

Still a further aspect of the present invention consists in the actually novel sulfonyl amino acid derivatives of formula I, i.e. those JNK inhibiting sulfonyl amino acid derivatives according to formula I that have not been disclosed by the prior art. As a matter of fact, some very few compounds according to formula I have been disclosed by Ragab A. et al. in *Indian J. Chem., Sec. B;* Org. Chem. Incl. Med. Chem., 1998, 37B(10), 1059-1062, without any medical indication, though. Said known compounds according to formula I of Ragab A. et al. are those wherein $Ar^1$ is a 4-chlorophenyl or a 2,4-bischlorophenyl residue; $Ar^2$ is phenyl; n=1; X is O, while the residues $R^1$, $R^2$, $R^3$ and $R^5$ are all H; $R^4$ is selected from H, $CH_3$, $CH_2$-$C_6H_4$—OH-4, $CH_2$—CH—$(CH_3)_2$ and $R^6$ is $CH_2$—$CO_2CH_3$.

Three further compounds have been disclosed by the CEREP company (www.cerep.fr) in as far as they have been mentioned in a company catalogue, without any medical indication, though.

Generally, the compounds according to formula I of the CEREP company are only those wherein $Ar^1$ is 4-chlorophenyl and X is O and $R^1$ is H, $Ar^2$ is a thienyl group, while in two compound the residues $R^1$, $R^2$, $R^3$, $R^5$ and $R^6$ are all H and $R^4$ is methyl or (4-hydroxyphenyl)ethyl. In the third CEREP compound, $R^1$, $R^3$, $R^5$ are H, $R^4$ is methyl, $R^2$ is propyl while $R^6$ is 2-methylphenyl.

Hence, the entirely novel sulfonyl amino acid derivatives according to formula I are those of formula I,

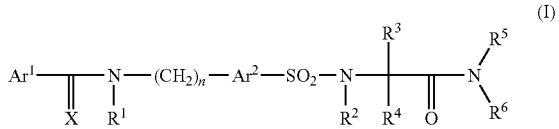

wherein the above identified known compounds of Ragab A. et al. and CEREP are excluded.

Still a further object of the present invention is a process for preparing the novel sulfonyl amino acid derivatives according to formula I which have been set out above.

The sulfonyl amino acid derivatives of this invention can be prepared from readily available starting materials using the following general methods and procedures. It will be appreciated that where typical or preferred experimental conditions (i.e. reaction temperatures, time, moles of reagents, solvents, etc.) are given, other experimental conditions can also be used unless otherwise stated. Optimum reaction conditions may vary with the particular reactants or solvent used, but such conditions can be determined by one skilled in the art by routine optimisation procedures.

According to a preferred method of synthesis, the sulfonyl amino acid derivatives according to formula I are prepared by first coupling an amine of formula II:

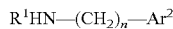   II whereby $Ar^2$ and $R^1$ are as defined above, with an acyl chloride of formula III:

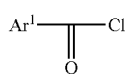   III whereby $Ar^1$ is as defined above, thus providing an amide according to formula IV:

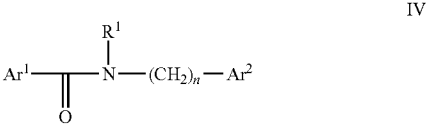   IV

Amines of formula II are either known compounds or can be prepared from known compounds by conventional procedures. Preferred amine as starting materials include thien-2-yl-methylamine, furan-2-yl-methylamine, pyridyl-2-ylmethylamine and the like.

The acyl chlorides of formula III are also commercially available or previously described compounds. Preferred acyl chlorides include 4-chlorobenzoyl chloride, 4-fluorobenzoylchloride, 4-trifluoromethylbenzoyl chloride and the like. If not known, the acid halide can be prepared by reacting the corresponding carboxylic acid with an inorganic acid halide, such as thionyl chloride, phosphorus trichloride or oxalyl chloride under conventional conditions.

Generally, this reaction is conducted upon using about 1 to 5 molar equivalents of the inorganic acid halide or oxalyl chloride, either neat or in an inert solvent, such as carbon tetrachloride, at temperature in the range of about 0° C. to about 80° C. for about 1 to about 48 hours. A catalyst, as N,N-dimethylformamide, may also be used in this reaction.

When an acyl halide is employed in the coupling reaction, it is typically reacted with amine II in the presence of a suitable base to scavenge the acid generated during the reaction. Suitable bases include, by way of example, triethylamine, diisopropylethylamine, N-methyl-morpholine and the like. Alternatively, an excess of amine II may be used to scavenge the acid generated during the reaction.

Alternatively, the carboxylic acid of compound III can be employed in the coupling reaction. The carboxylic acid of III are usually commercially available reagents or can be prepared by conventional procedures.

The coupling reaction of carboxylic acid of III (i.e. the acyl chloride) is conducted upon using any conventional coupling reagent including, for example, carbodiimides such as dicyclohexylcarbodiimide, N-(3-Dimethylaminopropyl)-N'-Ethylcarbodiimide and other promoting agents, such as N,N-carbonyl-diimidazole or PyBOP. This reaction can be conducted with or without the use of well known additives such as N-hydroxysuccinimide, 1-hydroxybenzotriazole, etc. which are known to facilitate the coupling of carboxylic acids and amines.

The coupling reaction using either acid halide III or its carboxylic acid is preferably conducted at a temperature of from about 0° C. to about 6° C. for about 1 to about 24 hours. Typically, the reaction is conducted in an inert aprotic polar solvent such as dimethylformamide, dichloromethane, chloroform, acetonitrile, tetrahydrofuran and the like using about 1 to about 5 molar equivalents of the amine based on the carboxylic acid or its acid halide. Upon completion of the reaction, the carboxamide IV is recovered by conventional methods including precipitation chromatography, filtration, distillation and the like.

The sulfonyl chlorides of formula V necessary for the preparation of the sulfonyl amino acids of formula I are either commercially available or prepared using conventional sulfonating methods:

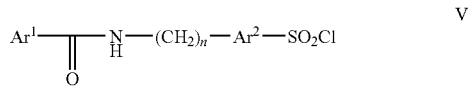

V

Preferred sulfonating reagent for use in this reaction is chlorosulfonic acid. Typically, the sulfonation reaction is conducted by treating the carboxamide of formula IV with about 5 to about 10 molar equivalent of the sulfonating reagent in an inert solvent, such as dichloromethane, at a temperature ranging from about −70° C. to about 50° C. Preferably, the addition of chlorosulfonic acid takes place at −70° C. and leads to the formation of the intermediate sulfonic acid. Increasing the temperature to 20° C. allows the formation of the sulfonyl chloride of formula V.

According to a further preferred method of preparation, notably in case that the above pointed out method leading to the preliminary synthesis of sulfonyl chloride of formula V is not applicable, the sulfonyl amino acids of this invention are alternatively prepared by the following steps:

Protection of the amine function of compounds of formula II;

Chlorosulfonylation of the aromatic group;

Formation of the sulfonyl amino acid function;

Deprotection of the protectiong group;

Acylation of the above generated free amine;

Amines of formula II are protected with a suitable protecting group of an amine moiety to provide intermediate compounds according to formula VI wherein P denotes any protecting group that a person skilled in the art would use in this context.

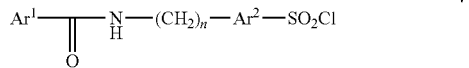

V

Numerous protecting groups P of the amine function as well as their introduction and removal, are well described in T. W. Green and G. M. Wuts, "*Protecting groups in Organic Synthesis,*" Third Edition, Wiley, N.Y., 1999, and references cited therein. Preferred are those protecting groups that are acids and bases stable and which can further be removed by using metal transition complexes such as palladium complexes, for example the allylcarbamate group (Alloc) or the N,N'-bisallyl group. A further preferred protecting group is the maleimide group which is stable in a wide range of experimental conditions.

The introduction of said groups can be performed by reacting the corresponding bisallylcarbonate anhydride or allylbromide or maleic anhydride in the presence of a base such as triethylamine, diisopropylethylamine, N-methylmorpholine and the like in a aprotic solvent such as N,N-dimethylformamide, dichloromethane, chloroform, acetronitrile, tetrahydrofuran and the like, at a temperature ranging from about 0° C. to about 80° C.

Compounds of formula VI are then sulfonated using a conventional very mild sulfonating procedure that allows the obtention of sulfonyl chloride of formula VII.

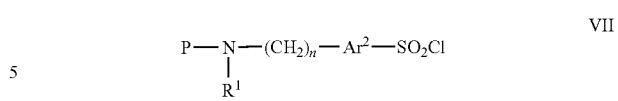

VII

Typically, protected amines VI are treated with a base such as n-butyllithium or tert-butyllithium under an inert atmosphere, in a polar aprotic solvent such as tetrahydrofuran, ether or dioxane at a temperature ranging from −70° C. to 0° C. for a period of time ranging from 15 minutes to 4 hours. The so formed anion is then treated with $SO_2Cl_2$ or more preferably with $SO_2$ by bubbling the gas into the reaction mixture at a temperature ranging from −70° C. to 20° C. during a time ranging from 5 minutes to 1 hour. The sulfonate obtained is then transformed "in situ" to the sulfonyl chloride of formula VII by contacting with N-chlorosuccinimide at a temperature ranging from 0° C. to 70° C.

Sulfonyl amino acid derivatives of formula I can be obtained from the corresponding above mentioned sulfonyl chloride V or VII using scheme 1 or 2 depicted below:

Scheme 1

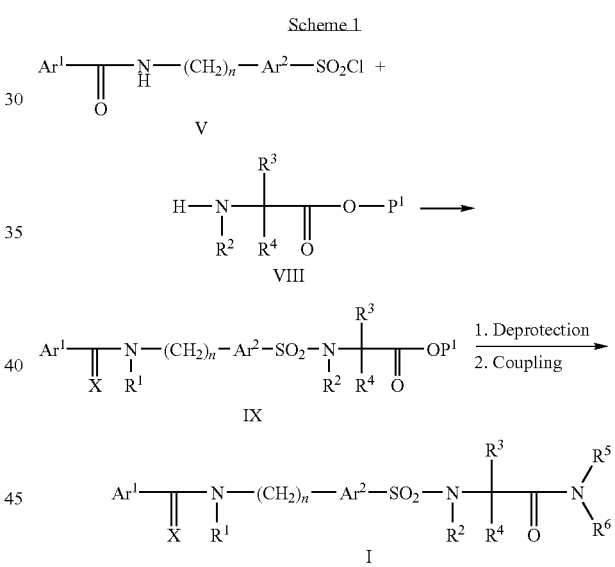

Scheme 2

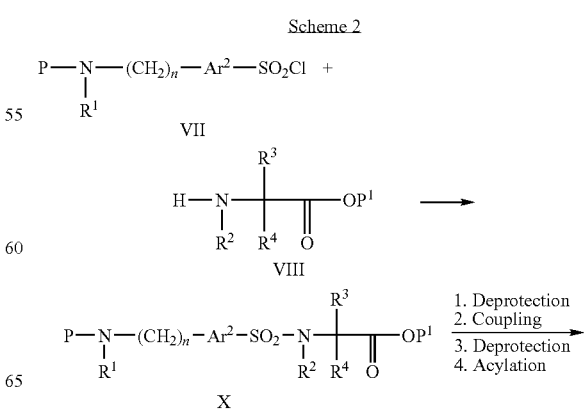

-continued

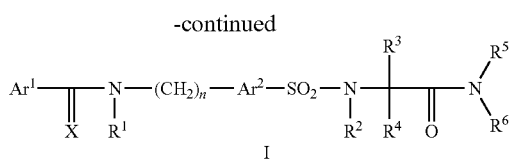

The protected amino acid derivative according to formula VIII are either commercially available or compounds that can be prepared by known procedures by one skilled in the art.

Numerous protecting groups of the carboyxlic function of an amino acid derivatives as well as their introduction and removal, are well described in T. W. Greene and G. W. Wuts, Protecting groups in Organic Synthesis, Third Edition, Wiley, N.Y., 1998, and references cited therein. Preferred are protecting groups that can be removed using acidic conditions such as alkyl esters and particularly tert-butylester.

The alkylation of the sulfonyl derivatives according to formula V or VII is then readily performed by reacting them with a protected amino acid derivative according to formula VIII in the presence of a suitable base to scavenge the acid generated during the reaction. Suitable bases include, by way of examples, triethylamine, diisopropylethylamine, N-methylmorpholine and the like. The reaction is preferably conducted in solvent such as N,N-dimethylformamide, dimethylsulfoxide, N-methylpyrrolidone, ethanol, acetonitrile at a temperature from about 0° to about 100° C.

The coupling reaction of the carboxylic acid function of the intermediate compounds IX or X, generated after deprotection, with an amine (commercially available or of known preparation) of type $R^5R^4NH$ is conducted according to known methods for the preparation of amides under the preferred conditions described above, thus leading to the compounds of general formula I.

The use of derivatives of formula X leads to sulfonyl amino acids that have to be deprotected and acylated to afford compounds of formula I according to Scheme 2.

An alternative method of preparation which has also to be considered as part of this invention, said method of preparation is described in Scheme 3 shown above.

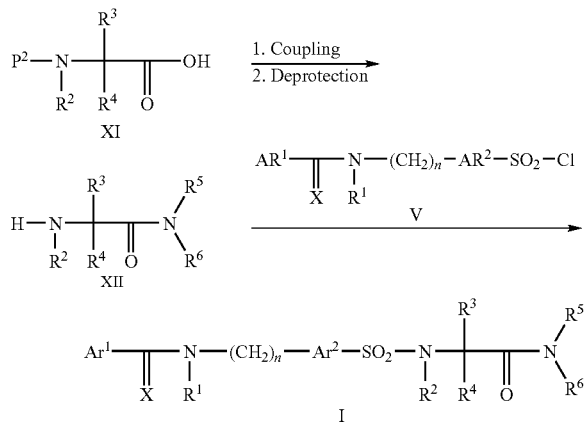

The protected amino acid derivatives according to formula IX are either commercially available or compounds that can be prepared by known procedures by one skilled in the art.

Numerous protecting groups of the amine function of the amino acid derivative as well as their introduction and removal, are well described in T. W. Greene and G. M. Wuts, Protecting groups in Organic Synthesis, Third Edition, Wiley, N.Y., 1998, and references cited therein. Preferred are protecting groups that can be removed using basic or acidic conditions such as respectively the Fmoc and the Boc groups.

The coupling reaction of the carboxylic acid function of compounds XI, with an amine (commercially available or of known preparation) of type $R^5R^4NH$ is conducted according to known methods for the preparation of amides under the preferred conditions described above.

The alkylation of the sulfonyl derivatives according to formula V is then readily performed by reacting them with the appropriate deprotected amino acid derivative XII in the presence of a suitable base to scavenge the acid generated during the reaction. Suitable bases include, by way of examples, triethylamine, diisopropylethylamine, N-methylmorpholine and the like. The reaction is preferably conducted in solvent such as N,N-dimethylformamide, dimethylsulfoxide, N-methylpyrrolidone, ethanol, acetonitrile at a temperature from about 0° to about 100° C.

If the above general synthetic methods are not applicable for the obtention of compounds of formula I, suitable methods of preparation known by a person skilled in the art should be used. For example, when $Ar^2$ is phenyl, one should start from commercially available 4-cyanophenyl sulfonyl chloride and applies conventional methods known by a person skilled in the art to reach sulfonamide derivatives of formula I.

A final aspect of the present invention is related to the use of the compounds according to formula I for the modulation of the JNK pathway, the use of said compounds for the preparation of pharmaceutical compositions for the modulation of the JNK pathway as well as the formulations containing the active compounds according to formula I. Said modulation of the JNK pathway is viewed as a suitable approach of treatment for various disorders. When employed as pharmaceuticals, the sulfonyl amino acid derivatives of the present invention are typically administered in the form of a pharmaceutical composition. Hence, pharmaceutical compositions comprising a compound of formula I and a pharmaceutically acceptable carrier, diluent or excipient therefore are also within the scope of the present invention. A person skilled in the art is aware of a whole variety of such carrier, diluent or excipient compounds suitable to formulate a pharmaceutical composition. Also, the present invention provides compounds for use as a medicament. In particular, the invention provides the compounds of formula I for use as JNK inhibitor, notably JNK1 and/or JNK2 and/or JNK3, for the treatment of disorders of the immune as well as the neuronal system of mammals, notably of humans, either alone or in combination with other medicaments.

The compounds of the present invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous use). Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

When employed as pharmaceuticals, the sulfonyl amino acids derivatives of the present invention are typically administered in the form of a pharmaceutical composition. Such compositions can be prepared in a manner well known in the pharmaceutical art and comprise at least one active compound. Generally, the compounds of this invention are administered in a pharmaceutically or pharmacological effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of the present invention can be administered by whole variety of routes including the oral, rectal, transdermal, subcutaneous, intravenous, intramuscular, and intranasal route. Depending on the intended route of delivery, the compounds are preferably formulated either as injectable or as oral compositions. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the sulfonyl amino acid compounds according to formula I are usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or non-aqueous vehicle with buffers, suspending and dispersing agents, colorants, flavors and the like. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharine; or a flavoring agent such as peppermint, methyl salicylate, or orange flavoring.

Injectable compositions are typically based upon injectable sterile saline or phosphate-buffered saline or other injectable carriers known in the art. As above mentioned, the sulfonyl amino acid compound of formula I in such compositions is typically a minor component, frequently ranging between 0.05 to 10% by weight with the remainder being the injectable carrier and the like.

The above described components for orally administered or injectable compositions are merely representative. Further materials as well as processing techniques and the like are set out in Part 8 of *Remington's Pharmaceutical Sciences*, 17th Edition, 1985, Marck Publishing Company, Easton, Pa., which is incorporated herein by reference.

The compounds of this invention can also be administered in sustained release forms of from sustained release drug delivery systems. A description of representative sustained release materials can also be found in the incorporated materials in *Remington's Pharmaceutical Sciences*.

In the following the present invention shall be illustrated by means of some examples which are not construed to be viewed as limiting the scope of the invention.

EXAMPLES

Example 1

4chloro-N-({5-[({2-[(2-{[3-chloro-5-(trifluoromethyl)pyridin-2-yl]amino}ethyl)amino]-2-oxoethyl}amino)sulfonyl]thien-2-yl}methyl)benzamide 1

4-Chloro-N-thiophen-2-ylmethyl-benzamide 1a

A solution of 4-chlorobenzoyl chloride (0.114 mol) in 50 ml dry $CH_2Cl_2$ is added over 30 min to a stirred solution of 2-aminomethyl-thiophene (0.137 mol) and $^iPr_2NEt$ (0.25 mol) in $CH_2Cl_2$ (200 ml) at 0° C. A white solid is formed and the reaction is allowed to warm to room temperature over 1 h. The mixture is diluted with 200 ml of $CH_2Cl_2$, washed twice with HCl aq. (0.1N) and dried over $MgSO_4$. Evaporation of the solvents affords 28 g (98%) of the title benzamide as a while solid: mp 153-54° C., $^1H$ NMR ($CDCl_3$) δ 7.9 (d, J=8.67 Hz, 2H), 7.58 (d, J=8.67 Hz, 2H), 7.44 (dd, J=3.77, 1.13 Hz, 1H), 7.22 (d, J=5.27 Hz, 1H), 7.16 (dd, J=3.39, 5.27 Hz, 1H), 6.62 (br d, 1H), 4.98 (d, J=5.65 Hz, 2H).

5-({[1-(4-Chloro-phenyl)-methanoyl]-amino}-methyl)-thiophene-2-sulfonyl chloride 1b Chlorosulfonic acid (20.1 ml, 198 mmol) in $CH_2Cl_2$ (80 ml) is added dropwise to a solution of 1a (10 g, 40 mmol) in $CH_2Cl_2$ (500 ml) at −80° C. The mixture is allowed to reach room temperature in 5 h. The reaction mixture is poured on ice and quickly extracted with $CH_2Cl_2$. The organic layer is dried over $MgSO_4$ and the solvent is evaporated to dryness which affords 8.8 g (63%) of desired sulfonyl chloride 1b; mp 133-35° C., $^1H$ NMR (DMSO) δ 9.21 (t, J=6.4 Hz, 1H), 7.87 (d, J=8.67 Hz, 2H), 7.53 (d, J=8.67 Hz, 2H), 6.91 (d, J=3.9 Hz, 1H), 6.77 (d, J=3.39 Hz, 1H), 4.53 (d, J=3.77 Hz, 2H).

[5-({[1-(4-Chloro-phenyl)-methanoyl]-amino}-methyl)-thiophene-2-sulfonylamino]-acetic acid tert-butyl ester 1c H-Gly-OtBu.HCl (263 mg, 1.57 mmol) is dissolved in 20 ml $CH_2Cl_2$. pH is adjusted to 9 using i-$Pr_2NEt$ as a base (537 μl, 3.14 mmol). To this solution is added dropwise 1b (500 mg, 1.43 mmol) in 10 ml DMF. The reaction is stirred overnight. 30 ml of $CH_2Cl_2$ are added and the organic phase washed with HCl (0.1N) and sat. NaCl sol. Drying over $MgSO_4$ and evaporating the solvent to dryness affords 1c (400 mg, 63%) as a white solid. mp °C., $^1H$ NMR (d6-DMSO) δ 9.34 (t, J=6.40 Hz, 1H), 8.25 (t, J=6.40 Hz, 1H), 7.89 (d, J=8.67 Hz, 2H), 7.56 (d, J=8.67 Hz, 2H), 7.41 (d, J=3.77 Hz, 1H), 7.05 (d, J=3.7 Hz, 1H), 4.62 (d, J=6.40 Hz, 2H), 3.59 (d, J=6.40 Hz, 2H), 1.3 (s, 9H).

[5-({[1-(4-Chloro-phenyl)-methanoyl]-amino}-methyl)-thiophene-2-sulfonylamino]-acetic acid 1d To a solution of 1c (400 mg, 0.9 mmole) in $CH_2Cl_2$ (10 ml) at 0° C. is added TFA (10 ml) and the reaction is stirred for 1 h at 0° C. and a further hour at room temperature. Evaporating the solvents to dryness gave 1d (300 mg, 86%) as a white solid. $^1H$ NMR (d6-DMSO) δ 9.34 (t, J=5.65 Hz, 1H), 8.20 (t, J=6.03 Hz, 1H), 7.89 (d, J=8.67 Hz, 2H), 7.56 (d, J=8.67 Hz, 2H), 7.43 (d, J=3.77 Hz, 1H), 7.05 (d, J=3.77 Hz, 1H), 4.63 (d, J=5.65 Hz, 2H), 3.59 (d, J=6.03 Hz, 2H).

4-chloro-N-({5-[({2-[(2-{[3-chloro-5-(trifluoromethyl)pyridin-2-yl]amino}ethyl)amino]-2-oxoethyl}amino)sulfonyl]thienyl-2-yl}methyl)benzamide 1

To a stirred solution of 1d (50 mg, 0.13 mmol) in CH$_2$Cl$_2$/DMF 2:1 (8 ml) are added i-Pr$_2$NEt to adjust pH to 7.5. DIC (18 mg, 0.14 mmol) and HOBt (19 mg, 0.14 mmol) are added and the solution is stirred for 30 min at room temperature. To this solution 1-(1-(3-Chloro-5-Trifluoromethyl)pyridine-ethylenediamine (34 mg, 0.14 mmol) in CH$_2$Cl$_2$ (3 ml) is added. The reaction mixture is allowed to stir for 4.5 h. 40 ml of CH$_2$Cl$_2$ are added and the organic phase is washed with HCl (0.1 N), sat. NaHCO$_3$, sat. NaCl and dried over MgSO$_4$. The crude product is purified by flash chromatography on silica gel using EtOAc/Hexane 8:2 as eluent to give 17 mg (21%) of 1. $^1$H NMR (d6-DMSO) δ 9.34 (t, J=6.03 Hz, 1H), 8.32 (brd, 1H), 8.04-8.14 (m, 2H), 7.95 (d, J=2.26 Hz, 1H), 7.88 (d, J=8.67 Hz, 2H), 7.54 (d, J=8.67 Hz, 2H), 7.43 (d, J=3.77 Hz, 1H), 7.28 (t, J=5.65 Hz, 1H), 7.06 (d, J=3.77 Hz, 1H), 4.63 (d, J=6.03 Hz, 2H), 3.36-3.48 (m, 4H)

Example 2

4-chloro-N-[(5-{[(2-{[2-({5-nitropyridin-2-yl}amino)ethyl]amino}-2-oxoethyl)amino]sulfonyl}thien-2-yl)methyl]benzamideamide 2

Diallyl-thiophen-2-ylmethylamine 2a

Allyl bromide (55 ml, 65.4 mmol) is added to a solution of 2-aminomethyl-thiophene (24 ml, 23.3 mmole) and i-Pr$_2$NEt (120 ml, 70.1 mmol) in CH$_2$Cl$_2$ (270 ml). The moderately exothermic reaction spontaneously reaches the reflux temperature after 1 h. The reaction is cooled by means of an ice bath and stirred for 14 h at rt. whereupon an undesired precipitate appeared. This precipitate (45 g) is removed by filtration. The organic layer is evaporated and diluted with EtOAc, whereupon more precipitate appears (45 g), which is removed by filtration. The EtOAc solution is filtered over SiO$_2$ and concentrated to give 36.1 g (80%) of the title diallylamine as a pale yellow oil: $^1$H NMR (CDCl$_3$) δ 7.25 (br. d, J=5.9 Hz, 1H), 6.98 (br. dd, J=5.1, 2.8 Hz, 1H), 6.94-6.92 (m, 1H), 5.99-5.86 (m, 2H), 5.29-5.18 (m, 4H), 3.85 (s, 2H), 3.16 (dd, J=6.3, 0.9 Hz, 4H).

5-Diallylaminomethyl-thiophene-2-sulfonyl chloride 2b

A solution of the allyl-protected thiophene 4a (6.2 g, 32.1 mmol) in Et$_2$O is cooled to −70° C. by means by an acetone/dry ice bath. A solution of t-BuLi in pentane (21.38 ml, 1.5M, 32.1 mmol) is added over 2 min whereupon the internal temperature momentarily rose to −50° C. and the mixture turned orange. After 10 min., SO$_2$ is bubbled for 2 min, which leads to the immediate formation of a thick precipitate. The reaction is allowed to reach 0° C., and a suspension of NCS (4.63 g, 32.1 mmol) in THF (20 ml) is added, whereupon the slurry turns purple. After 45 min at rt., the mixture is filtered over SiO$_2$, eluting with EtOAc. Evaporation, dilution with EtOAc:hexane 1:5 and filtration over SiO$_2$ gives the 5.0 g (53%) of the title sulfonyl chloride as a pale brown oil which is used without further purification.

2-(5-Diallylaminomethyl-thiophene-2-sulfonylamino)-[2-(5-nitro-pyridin-2-ylamino)ethyl]-acetamide 2c Preparation of 2c is performed as described above by first adding Glycine tert-butylester hydrochloride to 2b and second coupling the resulting deprotected intermediate with N-(5-nitro-pyridin-2-yl)-1,2-ethylenediamine.

2-(5-aminomethyl-thiophen-2-sulfonylamino)-[2-(5-nitro-pyridin-2-ylamino)-ethyl]-acetamide 2d A solution of the bisallylamine 2c (7.25 mmol), N,N'-dimethylbarbituric acid (NDMBA 2.8 g, 18.1 mmol), and Pd(PPh$_3$)$_4$ (148.8 mg, 0.13 mmol) in CH$_3$Cl$_2$ is degassed by bubbling argon for 10 min. The reaction mixture for 3 h at r.t. whereupon the desired amine 2d precipitates as its NDMBA salt. The mixture is diluted with EtOAc (200 ml) and hexane (200 ml) and washed with water (3×50 ml). The crude compound 2D is pure enough to be used in the next step without further purification.

4-chloro-N-[(5-{[(2-{[2-({5-nitropyridin-2-yl}amino)ethyl]amino}-2-oxoethyl)amino]sulfonyl}thien-2-yl)methyl]benzamide 2

A 20 mg/ml solution of the 2-aminomethyl-thiophene 2d in pyridine:CH$_2$Cl$_2$ 1:4 is cooled to −40° C. and treated for 1 h with 0.8 equiv. of 4-chlorophenyl sulfonyl chloride. The reaction mixture is brought to room temperature over 30 min. Evaporation, dilution in CH$_3$CN, filtration over a SiO$_2$ pad, and evaporation affords the desired amide 2. MS m/z APCI: 636 (M+1), 634 (M−1). Anal. HPLC: Rt=15.51 min (method c, see below)

Upon using the procedures described in the above examples 1-2 and the appropriate starting material and reagents, the following additional sulfonyl amino acid derivatives of formula I could be obtained:

The following table provides HPLC data and mass spectroscopy data of the mentioned examples.[1,2]

| Example | Name | Rt HPLC | Purity | Gradient HPLC | Mass M + 1 | Mass M |
|---|---|---|---|---|---|---|
| 3 | 4-chloro-N-({5-[({2-oxo-2-[(2-{[3-(trifluoromethyl)pyridin-2-yl]amino}ethyl)amino]ethyl}-amino)sulfonyl]thien-2-yl}methyl)benzanmide | 14 | 98 | c | 576 | 574 |
| 4 | 4-chloro-N-({5-[({2-oxo-2-[(2-{[5-(trifluoromethyl)pyridin-2-yl]amino}ethyl)amino]ethyl}-mino)sulfonyl]thien-2-yl}methyl)benzamide | 12 | 94 | b | 576 | 574 |
| 5 | N-({5-[({2-[(2-[4-(1H-1,2,3-benzotriazol-1-yl)piperidin-1-yl]-2-oxoethyl}amino)sulfonyl]thien-2-yl}-methyl)-4-chlorobenzamide | 11 | 90 | b | 573 | 571 |
| 6 | 4-chloro-N-[(5-{[(2-oxo-2-{3-[(trifluoromethyl-)sulfonyl]anilino)ethyl)amino]sulfonyl}thien-2-yl)methyl]benzamide | 6 | 91 | a | 596 | 594 |

Example 7

Preparation of a Pharmaceutical Formulation

The following formulation examples illustrate representative pharmaceutical compositions according to the present invention being not restricted thereto.

Formulation 1—Tablets

A sulfonyl amino acid compound of formula I is admixed as a dry powder with a dry gelatin binder in an approximate 1:2 weight ration. A minor amount of magnesium stearate is added as a lubricant. The mixture is formed into 240-270 mg tablets (80-90 mg of active sulfonyl amino acid compound per tablet) in a tablet press.

Formulation 2—Capsules

A sulfonyl amino acid compound of formula I is admixed as a dry powder with a starch diluent in an approximate 1:1 weight ratio. The mixture is filled into 250 mg capsules (125 mg of active sulfonyl amino acid compound per capsule).

[1] HPLC conditions: C8 Symmetry a-MeCN, 0.09% TFA, 0 to 100% (10 min)
HPLC conditions: C18 b-MeCN, 0.09% TFA, 0 to 100% (20 min), c-MeCN, 0.09% TFA, 0 to 100% (30 min).
[2] Mass spectrum APCI Formulation 3—Liquid A sulfonyl amino acid compound of formula I (1250 mg), sucrose (1.75 g) and xanthan gum (4 mg) are blended, passed through a No. 10 mesh U.S. sieve, and then mixed with a pre-viously prepared solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

A sulfonyl amino acid compound of formula I is admixed as a dry powder with a dry gelatin binder in an approximate 1:2 weight ratio. A minor amount of magnesium stearate is added as a lubricant. The mixture is formed into 459-900 mg tablets (150-300 mg of active sulfonamide compound) in a tablet press.

Formulation 5—Injection

A sulfonyl amino acid compound of formula I is dissolved in a buffered sterile saline injectable aqueous medium to a concentration of approximately 5 mg/ml.

Example 8

Biological Assays

JNK 2 and 3 in vitro assays: JNK 2 and/or 3 assays are performed 96 well MTT plates, by incubation of 0.5 µg of recombinant, pre-activated GST-JNK2 with 1 µg of recombinant, biotinylated GST-c-Jun and 2 µM $^{33}\gamma$-ATP (2 nCi/µl), in the presence or absence of sulfonyl amino acid inhibitors and in a reaction volume of 150 µl containing 50 mM Tris-HCl, pH 8.0; 10 mM $MgCl_2$; 1 mM Dithiothreitol, and 100 µM $NaVO_4$. The incubation is carried for 120 min. at R.T and stopped up by addition of 200 µl of a solution containing 250 µg of Streptavidine-coated SPA beads (Amersham, Inc.)*, 5 mM EDTA, 0.1% Trinton X-100 and 50 µM ATP, in phosphate saline buffer. After incubation for 60 minutes at RT, beads are sedimented by centrifugation at 1500×g for 5 minutes, resuspended in 200 µl of PBS containing 5 mM EDTA, 0.1% Triton X-100 and 50 µM ATP and the radioactivity measured in a scintillation β counter, following sedimentation of the beads as described above. By substituting GST-c-Jun for biotinylated GST-$_1$ATF$_2$ or myelin basic protein, this assay can be used to measure inhibition of preactivated p38 and ERK MAP Kinases, respectively.

Biological Results

The activities of the sulfonyl amino acid derivatives according to formula I were assessed using the above described biological assays. Representative values are given in the table shown below:

| Example | JNK3 | JNK2 | p38 | ERK2 |
|---------|------|------|-----|------|
| 1       | 1.2  | 2.7  | >30 | >30  |
| 6       | 0.64 | 1.3  | >30 | >30  |

The values indicated in respect to JNK2 and 3, p38 and ERK2 refer to the $IC_{50}$ (µM), i.e. the amount necessary to achieve 50% inhibition of said target (e.g. JNK2). AS# denotes on exemplary test compound as set out with its number in the above examples. From the above table it could be derived that said test compounds according to formula I do have a significant effect both on JNK2 and 3, but virtually no effect onto p38 and ERK2, thus delivering a quite selective inhibitory effect.

Sympathetic Neuron Culture and Survival Assay:

Sympathetic neurons from superior cervical ganglia (SCG) of newborn rats (p4) are dissociated in dispase, plated at a density of $10^4$ cells/cm$^2$ in 48 well MTT plates coated with rat tail collagen, and cultured in Leibowitz medium containing 5% rat serum, 0.75 µg/ml NGF 7S (Boehringer Mannheim Corp., Indianapolis, Ind.) and arabinosine $10^5$ M. Cell death is induced at day 4 after plating by exposing the culture to medium containing 10 µg/ml of anti NGF antibody (Boehringer Mannheim Corp., Indianapolis, Ind.) and no NGF or arabinosine, in the presence or absence of sulfonyl amino acid inhibitors. 24 hours after cell death induction, determination of cell viability is performed by incubation of the culture for 1 hour, at 37° C. in 0.5 mg/ml of 3-(4,5-dimethylthiazol-2-yl)2,5 diphenyl tetrazolium bromide (MTT). After incubation in MTT cells are resuspended in DMSO, transferred to a 96 MTT plate and cell viability is evaluated by measuring optical density at 590 nm.

The results of this assay with various test compounds demonstrate that compounds of Formula I are rescuing neurons from cells death (% neurons alive between 10 and 80)

IL-2 Release Assay:

Jurkat cells, a human T cell leukemia cell line (American Type Culture Collection #TIB 152) were cultured in RPMI 1640 medium (Gibco, BRL) supplemented with 10% of heat-activated FCS, Glutamine and Penstrep. The cell suspension in the medium is diluted to give $2.10^6$ cells/mL. The cells were plated ($2.10^5$ cells/well) on a 96-well plate containing different concentration of test compound (final concentration of compounds 10, 3, 1, 0.3, 0.1 µM). This mixture is incubated 30 minutes at 37° C. in a humidified $CO_2$ atmosphere. Cells were then treated with 10 ul PMA+Ionomycine (0.1 µM and 1 µM final concentration) in all wells except negative control. In wells without compounds, 10 µl of RPMI 2% DMSO (=0.1% final) is added. Cells are incubated 24 hours at 37° C. and then the supernatant harvested (freeze at −20° C. if not used the same day) prior to performing IL-2 ELISA test on the supernatant.

IL-2 ELISA Assay:

IL-2 release into the medium by PMA+Iono-stimulated Jurkat cells, in presence or absence of test compounds is assayed by ELISA. Following the procedure described below Solutions
  Wash buffer: PBS-Tween 0.05%
  Diluent: PBS-Tween 0.05%
  Substrate solution: Citric acid 0.1M/$Na_2HPO_4$ 0.1M
  Stop solution: $H_2SO_4$ 20%

Matched Antibody pairs/standard:
  From R&D Systems
    Monoclonal anti-human IL-2 antibody (MAB602) (capture)
    Biotinylated anti-human IL-2 antibody (BAF202) (detection)
    Recombinant human IL-2 (202-IL-010) (standard)

Plate preparation

Transfer 100 µl capture antibody diluted in PBS at 5 µg/mL into a 96 well ELISA plate and incubate overnight at room temperature.

Aspirate each well and wash 3 times with Wash buffer. After the last wash, damp the plate.
 1. Saturate with 200 µl PBS-10% FCS. Incubate 1 hour at room temperature.
 2. Repeat wash step 2.

Assay procedure
 1. Add 100 µl of sample or standard (2000, 1000, 500, 250, 125, 62.5, 31.25 pg/mL) and incubate 2 hours at room temperature.
 2. Wash 3 times.
 3. Add 100 µl of biotinylated anti-human IL-2 at 12.5 ng/mL. Incubate 2 hours at room temperature.
 4. Wash 3 times.
    Add 100 µl streptavidin-HRP (Zymed #43-4323) at 1:10'000. Incubate 30 minutes at room temperature.
 6. Wash 3 times.
 7. Add 100 µl substrate solution (ctirc acid/$Na_2HPO_4$ (1:1)+$H_2O_2$ 1:2000+OPD). Incubate 20-30 minutes at room temperature.
 8. Add 50 µl of stop solution to each well.
 9. Determine optical density using a microtiter plate reader set to 450 nm with correction at 570 nm.

The result of this assay shows that various test compounds decrease the production of IL-2 of more than 30%@3 uM.

C-Jun Reporter Assay

Cell culture

Hlr c-Jun HeLa cells are cultured in DMEM High Glc supplemented with 10% FCS (Sigma), 2 mM Glutamine (Gibco), P/S, Hygromycin b 100 µg/mL and G418 250 µg/mL Cull culture preparation Cell Banks The cells are stored frozen in cryotubes under liquid nitrogen, as 1.8 mL volumes of cell suspension in culture medium containing 10% dimethyl sulfoxide.

Cells are kept in culture for no more than 20 passages.

Cell culture thawing

When necessary, frozen vials of cells are thawed rapidly at 37° C. in a water bath by gently swirling up to semi-complete thawing. Then the cell suspension are added to 10 mL of culture medium.

The cell suspension is then centrifuged for 5 minutes at 1200 rpm, the supernatant is removed and the cell pellet reconstituted in the medium and add to a 175 $cm^2$ flask containing 25 mL medium. The flasks are incubated at 37° C. in an atmosphere of 5% $CO_2$.

Cell passage

The cells are serially subcultured (passaged) when 80% confluent monolayers have been obtained.

The medium of each flask is removed and the monolayer is washed with 10-15 mL of phosphate buffer solution (PBS).

Trypsin-EDTA solution is added to the cell monolayer, incubated at 37° C. and tapped gently at intervals to dislodge the cells. Complete detachment and disaggregation of the cell monolayer is confirmed by microscopy examination. The cells are then resuspended in 10 mL of complete medium and centrifuged for 5 minutes at 1200 rpm. The supernatant are discarded, the cells are resuspended in culture medium and diluted ⅕ in 175 $cm^2$ flasks.

Day 0 morning

Prepare cells for transfections

The cells from flasks of near-confluent cultures are detached and disaggregated by treatment with trypsin as described above.

The cells are resuspended in culture medium and counted.

The cell suspension are diluted with medium to give about $3.5 \times 10^6$ cells/mL and 1 mL µl of cell suspension are put onto 2 10 cm culture dishes containing 9 mL of culture medium. The plates are incubated at 37° C. in a humidified atmosphere of 5% $CO_2$ in air Day 0 evening Transfections
  Control: 0.2 µg p TK Renilla, 5.8 µg pBluescript KS, 500 µl OPTIMEM (GIBCO), 18 µl Fugene 6
  Induced: 0.1 µg pMEKK1, 0.2 µg pTK Renilla, 5.7 µg pBluescript KS, 500 µl OPTIMEM (GIBCO), 18 µl Fugene 6 30' RT The transfection mixture is added to the plated cells. The plates were incubated over night at 37° C. in a humidified atmosphere of 5% $CO_2$ in air Day 1

A 96 wells plate containing 100 µl of culture medium per well is prepared

Negative control (vehicle): 2 µl of DMSO is added to the 100 µl (in triplicate).

Compound: 2 µl of Hit compound stock dilution ware added to the 100 µl (in triplicate). The transfected cells are trypsinised and ressuspended in 12 mL of culture medium. 100 µl of the dilution was added to each of the 96 wells plate. The plate is incubated over night at 37° C. in a humidified atmosphere of 5% $CO_2$ in air Hit compound dilutions Hit compound stock concentrations are the following:
  3, 1 and 0.1 mM in 100% DMSO.

Day 2

Test procedure

Dual-Luciferase™ Reporter Assay System (Promega)

The medium is removed from the plate and the cells washed two times with 100 µl PBS Completely remove the rinse solution before applying PLB reagent. Dispense into each culture well 5 µl of 1×PLB. Place the culture plates on a rocking platform or orbital shaker with gentle rocking/shaking to ensure complete and even coverage of the cell monolayer with 1×PLB. Rock the culture plates at room temperature for 15 minutes. Transfer 20 μl of the lysate into a white opaque 96 wells plate. Read in a luminometer.

Inject 50 μl of Luciferase Assay Reagent II wait 5", read 10"

Inject 50 μl of Stop & Glo® Reagent wait 5", read 10"

Check RLU Luciferase/RLU Renilla*1000

The result of this assay shows that various test compounds inhibit more than 20% of the activity of JNK@10 uM.

LPS Induced Endotoxin Shock in Mice

The ability of the JNK inhibitors described in formula I to significantly reduce the level of inflammatory cytokins induced by LPS challenge was assessed using the following protocol:

LPS (S. abortus-Glanaos Lab.-) was injected (200 μg/kg, i.v.) to Male C57BL/6 to induce endotoxin shock and compounds (0.1, 1, 10 mg/kg) or NaCl (200 uM) were injected intravenously (10 mL/kg) 15 min before the LPS challenge. Heparinized blood was obtained from the orbital sinus at different time points after the LPS challenge, and the blood was centrifuged at 9,000 rpm for 10 min at 4° C. to collect supernatant for the measurement of cytokines production by mouse ELISA kit such as IFNγ (Duoset R&D Ref. DY485).

The test compounds displayed considerable capability to reduce inflammatory related cytokines.

Global Inschemia in Gerbils

The ability of the JNK inhibitors described in formula I to protect cell death during a stroke event was assessed using the following protocol:

1 Method

Surgery

Anesthesia: halothane or isofluorane (0.5-4%).

Sheaving of the gorge and incision of the skin.

The common carotid arteries (left and right) are free from tissue.

Occlusion of the arteries using Bulldog microclamps during 5 min.

Disinfection of the surgery plan (Betadin®) and suture of the skin (Autoclip® ou Michel's hooks).

Stabulation of the animals under heating lamp until awake.

Stabulation of the animals in the animalry in individual cages.

Sacrifice of the animals 7 days after ischemia (Decapitation or overdose of pentobarbital).

Sampling of the brain.

Histological parameters

Freezing of the brain in isopentane (−20° C.)

Slicing of the hippocampus using a cryo-microtone (20 μm).

Staining with cresyl voilet and/or TUNEL method

Evaluation of the lesions (in CA1/CA2 subfields of the hippocampus)

Gerhard & Boast score modified or

Cell counting in the CA1/CA2

Biochemical parameters

Microdissection of the cerebral structures

Parameters determined: DNA fragmentation, lactate, calcium penetration.

Analytical methods: ELISA, colorimetry, enzymology, radiometry.

2 Treatment

Administration of the test article or the vehicle: 15 min after reperfusion (5-10 min after the recovery of the anehsthesia).

Standard protocol 50 animals: 5 groups of 10 (group A: control, groups B-D: test article at 3 doses and group E: reference compound (ketamine 3×120 mg/kg, ip or Orotic acid 3×300 mg/kg, ip).

The test compounds displayed considerable capability to protect from neuronal apoptosis during induced global ischemia.

The invention claimed is:

1. A compound which is:

4-chloro-N-({5-[({2-[(2-{[3-chloro-5-(trifluoromethyl) pyridin-2-yl]amino}ethyl)amino]-2-oxoethyl}amino) sulfonyl]thien-2-yl}methyl)benzamide, 4-chloro-N-[(5-{[(2-{[2-({5-nitropyridin-2-yl}amino) ethyl]amino}-2-oxoethyl)amino]sulfonyl}thien-2-yl) methyl]benzamide, 4-chloro-N-({5-[({2-oxo-2-[(2-{[3-(trifluoromethyl)pyridin-2-yl]amino}ethyl)amino]ethyl}amino)sulfonyl] thien-2-yl}methyl)benzamide, 4-chloro -N-({5-[({2-oxo-2-[(2-{[5-(trifluoromethyl)pyridin-2-yl]amino}ethyl)amino]ethyl}amino)sulfonyl] thien-2-yl}methyl)benzamide, or 4-chloro-N-[(5-{[(2-oxo-2-{3-[(trifluoromethyl)sulfonyl] anilino}ethyl)amino]sulfonyl}thien-2-yl)methyl]benzamide.

2. A pharmaceutical composition comprising at least one compound according to claim 1 and a pharmaceutically acceptable carrier, diluent or excipient.

3. 4-chloro-N-({5-[({2-[(2-{[3-chloro-5-(trifluoromethyl) pyridin-2-yl]amino}ethyl)-amino]-2-oxoethyl}amino)sulfonyl]thien-2-yl}methyl)benzamide.

4. A pharmaceutical composition comprising 4-chloro-N-({5-[({2-[(2-{[3-chloro-5-(trifluoromethyl)pyridin-2-yl] amino}ethyl)-amino]-2-oxoethyl}amino)sulfonyl]thien-2-yl}methyl)benzamide and a pharmaceutically acceptable carrier, diluent or excipient.

* * * * *